(12) United States Patent
Bowden et al.

(10) Patent No.: US 6,323,343 B1
(45) Date of Patent: Nov. 27, 2001

(54) PROCESS FOR THE PREPARATION OF 8-AZABICYCLO(3.2.1)OCTANE DERIVATIVES

(75) Inventors: Martin Charles Bowden; Stephen Martin Brown, both of Huddersfield; Douglas John Smith; Trevor Robert Perrior, both of Bracknell, all of (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/555,463
(22) PCT Filed: Dec. 7, 1998
(86) PCT No.: PCT/GB98/03633
  § 371 Date: May 30, 2000
  § 102(e) Date: May 30, 2000
(87) PCT Pub. No.: WO99/29690
  PCT Pub. Date: Jun. 17, 1999

(30) Foreign Application Priority Data

Dec. 11, 1997 (GB) .................................................. 9726251
Apr. 30, 1998 (GB) .................................................. 9809291

(51) Int. Cl.[7] ...................... C07D 451/02; C07D 451/04
(52) U.S. Cl. ............................................ 546/127; 546/124
(58) Field of Search .................................. 546/124, 132, 546/127

(56) References Cited

U.S. PATENT DOCUMENTS 3,120,537   2/1964   Archer et al. ........................ 546/132

FOREIGN PATENT DOCUMENTS

96/37494   11/1996   (WO) .
97/13770   4/1997   (WO) .

OTHER PUBLICATIONS

C.J. Swain, et al., Novel 5–HT$_3$ Antagonists: Indol–3–ylspiro(azabicyloalkane–3,5'(4'H)–oxazoles), 35 Journal of Medicinal Chemistry, 1019–1031 (1992).

J.E. Dewhurst et al., Mass Spectra of Some Tropane and Tropidine Derivatives, 9 Journal of Heterocyclic Chemistry, 507–511 (Jun. 1972).

E. Galvez et al., Synthesis and Structural Study of N–Ethylnortropane–3–Spiro–5'–Oxazolidine–2'–Dione and its Hydrochloride, 99 Journel of molecular structure, 247–258 (1983).

C. Burgos et al., Synthesis and Structural, Conformational and Pharmacological Study of Some Esters Derived From 3–βhydroxytropane–3–α–carboxylic Acid, 301 Journal of Molecular Structure, 95–105 (1993).

P. Nemes et al., Synthesis and Stereochemistry of Epimeric 3–Benzoyltronpanes, 104 Acta Chimica Academiae Scientiarum Hungaricae, 235–242 (1980).

C.L. Zirkle et al., 3–Substituted Tropane Derivatives, 27 Journal of Organic Chemistry, 1269–1279 (Jul. 1962).

*Primary Examiner*—Alan L. Rotman
(74) *Attorney, Agent, or Firm*—Hale and Dorr LLP

(57) ABSTRACT

A process for preparing a compound of formula (IV), wherein $R^1$ is $C_{1-4}$alkyl, $CH_2(C_{1-3}$haloalkyl), benzyl, $CH_2(C_{2-5}$akenyl or $CH_2(C_{2-5}$alkynyl), which comprises reducing a compound of formula (III). Compounds of formula (IV) are agrochemical intermediates.

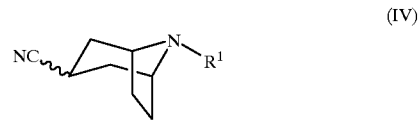

(IV)

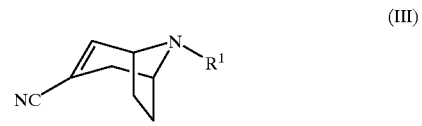

(III)

7 Claims, No Drawings

PROCESS FOR THE PREPARATION OF 8-AZABICYCLO(3.2.1)OCTANE DERIVATIVES

CROSS-REFERENCE

This application is a 371 of PCT/GB98/03633 filed Dec. 7, 1998.

The present invention concerns a process for preparing 3-cyano-8-substituted-8-azabicyclo[3.2.1]octanes are useful as intermediates for certain insecticides (see, for example, WO 96/37494).

The present invention provides a process for preparing a compound of formula (IV), wherein $R^1$ is $C_{1-4}$ alkyl, $CH_2$ ($C_{1-3}$ haloalkyl), benzyl, $CH_2(C_{2-5}$ alkenyl) or $CH_2(C_{2-5}$ alkynyl), which comprises reducing a compound of formula (III). It is preferred that the reduction is effected using a mixture of an alcohol (preferably methanol) and a suitable metal (such as magnesium); by using a borohydride (such as an alkali metal borohydride, for example lithium or sodium borohydride) in an alcohol (preferably methanol) and, optionally, in the presence of a suitable amine (such as pyridine); or by catalytic hydrogenation (for example using a catalyst comprising palladium at a suitable pressure).

In one particular aspect the present invention provides a process for preparing a compound of formula (IV), wherein $R^1$ is as defined above, comprising the steps:
i. dehydrating a compound of formula (II) to give a compound of formula (III); and,
ii. reducing a compound of formula (III).

For example, a compound of formula (II) can be dehydrated by the use of a suitable acid chloride (such as thionyl chloride, phosphorus oxychloride, sulphuryl chloride or phosgene), in the presence of a suitable amine having a pKa in the range 3–11 (especially 4–6) [such as a tri($C_{1-4}$ alkyl) amine (such as triethylamine or diisopropylethylamine), pyridine, a ($C_{1-4}$ alkyl)pyridine (such as (α-picoline, β-picoline or γ-picoline), a di($C_{1-4}$ alkyl)-aminopyridine (such as 4-dimethylaminopyridine), quinoline, isoquinoline or a di($C_{1-4}$ alkyl)aniline (such as N,N-dimethylaniline)], optionally in a solvent [such as an excess of amine, or an aprotic or polar aprotic solvent for example an aromatic hydrocarbon (especially toluene, a xylene, fluorobenzene or chlorobenzene), acetonitrile, an ether (especially tetrahydrofuran or dioxan) or a chlorinated aliphatic solvent (especially dichloroethane)], at a suitable temperature in the range 0–110° C. (especially 10–40° C.).

It is preferred that a compound of formula (II) is dehydrated by the use of a suitable acid chloride (such as thionyl chloride or phosphorus oxychloride) in the presence of a suitable amine (preferably pyridine).

In another aspect the present invention provides a process for preparing a compound of formula (IV), wherein $R^1$ is as defined above, comprising the steps:
i. cyanating a compound of formula (I) to give a compound of formula (II);
ii. dehydrating a compound of formula (II) to give a compound of formula (III); and,
iii. reducing a compound of formula (III).

It is preferred that the compound of formula (I) is cyanated by reacting it with hydrogen cyanide in the presence of a suitable base. It is preferred that the hydrogen cyanide is prepared in situ (for example by the reaction of an inorganic cyanide (such as an alkali metal cyanide, for example sodium cyanide or potassium cyanide) with an acid (such as an organic acid (for example acetic acid) or a strong mineral acid (for example hydrochloric acid)). Suitable bases include the cyanide anion (for example from the presence of an inorganic cyanide (such as an alkali metal cyanide, for example sodium cyanide or potassium cyanide)). The cyanation reaction may be carried out in the presence of ammonium chloride.

It is preferred that the cyanation of the compound of formula (I) is carried out in the presence of a solvent or mixture of solvents. A preferred solvent is water, and preferred mixtures of solvents include mixtures of water with an ether (such as diethyl ether or methyl tert-butyl ether), an alcohol (such as methanol or n-butanol) or an aromatic solvent (such as toluene).

Alkyl groups of $R^1$ may be straight or branch chains are, for example, methyl, ethyl, n-propyl or iso-propyl.

The haloalkyl moiety of the group $CH_2(C_{1-3}$ haloalkyl) is preferably alkyl optionally substituted with chlorine or fluorine and is, for example, 2,2,2-trifluoromethyl or 2,2-difluoromethyl. (Thus, $CH_2(C_{1-3}$ haloalkyl) is, for example, 2,2,2-trifluoroethyl or 2,2-difluoroethyl.)

Alkenyl and alkynyl groups are, for example, vinyl, allyl or propargyl.

A compound of formula (II) can be prepared by adding a suitable inorganic cyanide (preferably potassium cyanide) to a mixture of a compound of formula (I) and a suitable mineral acid (preferably hydrochloric acid or sulphuric acid) and, optionally, ammonium chloride, at a suitable temperature (preferably in the range −20–20° C., such as at about 0° C.) and allowing the reaction to take place at this temperature. Suitable solvents for this reaction include water or a mixture of water and an organic solvent (such as an ether (for example diethyl ether)).

In one aspect a compound of formula (II) can be prepared from a compound of formula (I) by the method described above wherein an excess of hydrogen cyanide is used for the preparation. The excess may be achieved by using an excess (such as between 1 and 2 (especially 1.1–1.8) equivalents) of acid and an excess (such as between 1 and 2 (especially 1.1–1.6) equivalents) of inorganic cyanide. In another aspect all the inorganic cyanide is added at the beginning of the preparation and the acid is added over a period of time during the course of the preparation. It is preferred that the acid is a strong mineral acid (especially hydrochloric acid or sulphuric acid) and that the inorganic cyanide is sodium cyanide or potassium cyanide.

In a further and preferred aspect a compound of formula (II) can be prepared by using an excess (such as 1–10, especially 2–7 equivalents) of a strong mineral acid (especially hydrochloric acid or sulphuric acid) and an excess (such as 1–12, especially 3–8 equivalents) of alkali metal cyanide (for example sodium cyanide or potassium cyanide) relative to the compound of formula (I). It is preferred that the process is operated at a temperature in the range −20–20° C., such as at about 0° C.

In another aspect, a mixture of a compound of formula (I) with a suitable mineral acid (preferably hydrochloric acid or sulphuric acid) in a suitable solvent (preferably water) is added over a period of time to an inorganic cyanide (for example sodium cyanide or potassium cyanide) during the course of the preparation of a compound of formula (II) at a suitable temperature (for example in the range −20–20° C., such as at about 0° C.).

Compounds of formula (II) can degrade over time. Degradation can be minimised by isolating the compound of formula (II) in a suitable organic solvent (such as an ether (for example diethyl ether or methyl tert-butyl ether) or an alcohol (for example methanol or n-butanol), and such solution can be used in the processing of a compound of formula (II) to a compound of formula (III). Alternatively, degradation can be minimised by adding a suitable stabilising agent (such as a small amount of concentrated sulphuric acid) to the compound of formula (II) prior to its isolation.

A compound of formula (III) can be prepared by adding a compound of formula of formula (II) to a mixture of phosphorus oxychloride and a suitable amine (such as pyridine) in a suitable solvent (which may be an excess of phosphorus oxychloride, or, when the amine is a liquid, may be an excess of the amine) and allowing the reaction to proceed at a suitably elevated temperature (such as between 50° C. and the boiling point of the solvent used).

For the dehydration of a compound of formula (II) it is preferred that an acid chloride is added to a mixture of a compound of formula (II) and an amine, preferably as <20° C.

A compound of formula (IV) can be prepared by adding a compound of formula (III) to a mixture of an alcohol (preferably methanol) and, optionally, a suitable amine (such as pyridine), and then adding a suitable borohydride (especially sodium borohydride) to the reaction mixture and allowing the reaction to proceed at a suitable elevated temperature (such as between 50° C. and the boiling point of the alcohol used).

Alternatively, a compound of formula (IV) can be prepared by adding magnesium to a mixture of a compound of formula (III) and an alcohol (especially methanol) and maintaining the temperature in the range −20–20° C. (especially at about 0° C.).

Alternatively, a compound of formula (IV) can be prepared by catalytic hydrogenation of a compound of formula (III) at room temperature and atmospheric pressure using a suitable catalyst (preferably palladium on carbon) in a suitable solvent or mixture of solvents selected from water, an alcohol (especially methanol or ethanol) or an aromatic solvent (especially toluene). Suitable solvent mixtures include: toluene and water; toluene, methanol and water; toluene and methanol; and ethanol and water.

Alternatively, and preferably, a compound of formula (IV) can be prepared by catalytic hydrogenation of a compound of formula (III) under substantially anhydrous conditions using palladium on carbon, palladium/barium sulphate, palladium/alumina, platinum oxide, Raney nickel or ruthenium on carbon as a catalyst (palladium on carbon is preferred), 0.5–5.0% equivalents of catalyst, at a temperature in the range 20–100° C. (especially 35–75° C.), at a pressure in the range 1–10 bar (especially 2–6 bar) and in the presence of a solvent or mixture of solvents. Preferred solvents are aromatic hydrocarbons (such as benzene, toluene, o-xylene, m-xylene or p-xylene) or an aliphatic alcohol (especially a $C_{1-6}$ aliphatic alcohol such as ethanol or tert-butanol). Preferred solvents are toluene or a mixture (such as about a 10:1 mixture) of toluene and tert-butanol.

In yet a further aspect the present invention provides a process for preparing a compound of formula (IV), wherein $R^1$ is as hereinbefore defined, comprising the steps:

i. reacting a compound of formula (I) with a mixture of an alkali metal cyanide (such as sodium cyanide or potassium cyanide) and a mineral acid (preferably hydrochloric acid or sulphuric acid) in water at ambient temperature to give a compound of formula (II);
ii. reacting a compound of formula (II) with thionyl chloride or phosphorus oxychloride in the presence of pyridine to give a compound of formula (III); and,
iii. reducing a compound of formula (III) by reacting it with hydrogen under substantially anhydrous conditions in the presence of a palladium on carbon catalyst at a temperature in the range 35–75° C. at a pressure in the range 2–6 bar and in the presence of an aromatic hydrocarbon solvent (preferably toluene or a xylene).

It is preferred that the mixture of an alkali metal cyanide and a mineral acid in (i) provides 3–10 equivalents of hydrogen cyanide relative to the amount of compound of formula (I) used.

A process as hereinbefore defined wherein $R^1$ is $CH_2(C_{1-3}$ haloalkyl) (especially $CH_2CF_3$ or $CH_2CHF_2$.

A compound of formula (A) can be prepared by reacting a compound of formula (IV) with a compound $R^2L$, wherein $R^2$ is pyridyl optionally substituted with halogen, $C_{1-4}$ alkyl, $C_{1-4}$ alkoxy, cyano, $C_{2-4}$ alkenyl or $C_{2-4}$ alkynyl, and L is a suitable leaving group (such as halogen or mesylate), in the presence of a suitable base. Thus, in a further aspect the present invention provides a compound of formula (A) when made by reacting a compound of formula (IV) (as prepared by a process as hereinbefore described) with a compound $R^2L$ in the presence of a suitable base.

In another aspect the present invention provides a compound of formula (A), wherein $R^1$ is $C_{1-4}$ alkyl, $CH_2(C_{1-3}$ haloalkyl), benzyl, $CH_2(C_{2-5}$ alkenyl) or $CH_2(C_{2-5}$ alkynyl), and $R^2$ is pyridyl optionally substituted with halogen, $C_{1-4}$ alkyl, $C_{1-4}$ alkoxy, cyano, $C_{2-4}$ alkenyl or $C_{2-4}$ alkynyl, when prepared by a process comprising the steps:

i. reducing a compound of formula (III), to form a compound of formula (IV); and,
ii. reacting a compound of formula (IV) with a compound $R^2L$, wherein L is a suitable leaving group (such as halogen or mesylate), in the presence of a suitable base.

In another aspect the present invention provides a compound of formula (II) or (III) wherein $R^1$ is $C_{1-4}$ alkyl, $CH_2(C_{1-3}$ haloalkyl), benzyl, $CH_2(C_{2-5}$ alkenyl) or $CH_2(C_{2-5}$ alkynyl).

In a still further aspect the present invention provides a compound of formula (II) or (III) wherein $R^1$ is 2,2,2-trifluoroethyl or 2,2-difluoroethyl.

In another aspect the present invention provides a process for preparing a compound of formula (II) wherein $R^1$ is as defined above, comprising contacting a compound of formula (V):

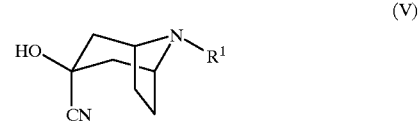

(V)

with a mixture of an alkali metal cyanide (especially sodium cyanide or potassium cyanide) and a strong mineral acid (preferably hydrochloric acid) in a suitable solvent (such as water). It is preferred that this process is conducted in the presence of sodium chloride. It is further preferred that the process is carried out at ambient (that is 10–35° C.) temperature.

The following Example illustrate the invention. Selected NMR data and mass spectral data are presented in the Examples. For NMR data, no attempt has been made to list every absorption. The following abbreviations are used throughout the Examples:

m = multiplet         ppm = parts per million
brs = broad singlet   t = triplet

-continued

| | |
|---|---|
| d = doublet | q = quartet |
| dd = double doublet | dt = double triplet |
| tt = triple triplet | DMF = N,N-dimethylformamide |
| THF = tetrahydrofuran | |

EXAMPLE 1

This Example illustrates the preparation of 3-cyano-8-(2,2,2-trifluoroethyl)-8-azabicyclo[3.2.1]octane.

Step 1

A 50 ml 2-necked round bottom flask was fitted with a pressure equalised dropping funnel, bubbler and magnetic stirrer. 8-(2,2,2-Trifluoroethyl)-8-azabicyclo[3.2.1]octan-3-one (5.23 g, 25 mmol) was charged to the reaction flask and suspended in water (5 ml). Hydrochloric acid (5 ml, 5M) was added followed by solid ammonium chloride (2.15 g) and the mixture stirred until the ammonium chloride had dissolved. The mixture was cooled to 0° C., a solution of potassium cyanide (5.031 g, 75 mmol) in water (7.5 ml) was added over 1 hour and the resulting mixture was then stirred at 0° C. for 2 hours during which time a solid precipitate formed. The precipitate was isolated by filtration and sucked dry for 10 minutes, to give 3-cyano-3-hydroxy-8-(2,2,2-trifluoroethyl)-8-azabicyclo[3.2.1]octane as an off-white solid (6.62 g).

Mass spectral data: 234 ($M^+$), 217, 207, 178, 164, 150, 110.

Step 2

An oven-dried 100 ml 3-necked round bottom flask was fitted with a reflux condenser, thermometer and magnetic stirrer and the apparatus filled with a nitrogen atmosphere. Phosphorous oxychloride (8.89 g, 58 mmol) and pyridine (44 ml) were charged and the mixture then cooled to −10° C. in an acetone/Drikold™ bath. 3-Cyano-3-hydroxy-8-(2,2,2-trifluoroethyl)-8-azabicyclo[3.2.1]octane (6.17 g, 26.4 mmol—assumed) was added in one portion and the resulting exotherm raised the reaction mass temperature to 28° C. The mixture was then heated to 80° C. and held at this temperature overnight. The reaction mass was cooled to ambient (precipitation occurred) and added to a stirred mixture of saturated aqueous sodium carbonate (200 ml) and ethyl acetate (200 ml). The layers were separated and the aqueous then extracted with ethyl acetate (2×200 ml). The combined organics were washed with brine (100 ml), dried ($Na_2SO_4$) and concentrated in vacuo to give 3-cyano-8-(2,2,2-trifluoroethyl)-8-azabicyclo[3.2.1]oct-2-ene (2.5 g, 35% yield).

$^1$H NMR ($CDCl_3$): δ1.60–2.40(m,5H), 2.60–2.80(m,1H), 3.10(q,2H), 3.45–3.65(m,2H), 6.75(m, 1H)ppm.

Mass spectral data: 216 ($M^+$), 201, 187, 164, 147, 118, 110.

Step 3

An oven-dried 10 ml round bottom flask was fitted with a reflux condenser and magnetic stirrer and the apparatus filled with a nitrogen atmosphere. 3-Cyano-8-(2,2,2-trifluoroethyl)-8-azabicyclo[3.2.1]oct-2-ene (0.216 g, 1 mmol) was charged to the flask followed by methanol (0.5 ml) and pyridine (1.5 ml) to give a solution. Sodium borohydride (0.046 g, 1.2 mmol) was added in a single portion and the mixture was heated to 80° C. The reaction was held at this temperature overnight, refluxed for 3 hours and then cooled to ambient. Saturated aqueous potassium dihydrogen phosphate (10 ml) was added to the reaction mass and the aqueous solution (pH7) was then extracted with ethyl acetate (3×10 ml). The combined organic layers were washed with brine (10 ml), dried ($Na_2SO_4$) and concentrated in vacuo to give 3-cyano-8-(2,2,2-trifluoroethyl)-8-azabicyclo[3.2.1]octane (0.22 g, 74% yield) as a mixture of epimers (12:1 equatorial:axial).

$^1$H NMR ($CDCl_3$) (equatorial isomer): δ1.50–2.15(m, 8H), 2.65–2.85(m,1H), 2.85(q,2H), 3.30–3.40(m,2H)ppm.

Mass spectral data: 218 ($M^+$), 199, 189, 164, 150.

EXAMPLE 2

This Example illustrates the preparation of 3-cyano-8-(2,2,2-trifluoroethyl)-8-azabicyclo[3.2.1]octane.

An oven-dried 50 ml round bottom flask was fitted with a reflux condenser and magnetic stirrer and the apparatus filled with a nitrogen atmosphere. 3-Cyano-8-(2,2,2-trifluoroethyl)-8-azabicyclo[3.2.1]oct-2-ene (0.26 g, 1 mmol) was charged to the reactor followed by methanol (10 ml). Magnesium turnings (1.0 g, 40 mmol) were added in a single portion and after an induction period of 0.25 hours, a vigorous reaction occurred which was moderated by cooling with an ice bath. The mixture was stirred at 0° C. for 1 hour, during which time the reaction mass thickened (due to magnesium methoxide formation), and was then allowed to warm to ambient. The reaction mixture was added to a solution of potassium dihydrogen phosphate (10 g) in water (40 ml) and stirred for 0.5 hour. Residual solid was removed by filtration and the aqueous filtrate was extracted with ethyl acetate (3×20 ml). The combined organic layers were washed with brine (20 ml), dried ($Na_2SO_4$) and concentrated in vacuo to give 3-cyano-8-(2,2,2-trifluoroethyl)-8-azabicyclo[3.2.1]octane (0.6 g, 72% yield) as a mixture of epimers (25:75 exo:endo).

$^1$H NMR ($CDCl_3$) (endo isomer): δ1.50–2.30(m,8H), 2.85(q,2H), 2.90(t,1H), 3.30–3.40(m,2H)ppm.

Mass spectral data: 218 ($M^+$), 199, 189, 164, 150.

EXAMPLE 3

This Example illustrates the preparation of 3-cyano-8-(2,2-difluoroethyl)-8-azabicyclo[3.2.1 ]octane.

Step 1

To a 500 ml 3-necked round bottom flask fitted with a still head (short path distillation) and a thermometer was charged 2,5-dimethoxytetrahydrofuran (21.7 g, 0.16 mol), hydrochloric acid (9.2 ml, 0.1 Molar) and water (125 ml). The mixture was heated to 120° C. and held at this temperature until 40 ml of distillate had been collected. The still head was replaced with a condenser and nitrogen atmosphere and the mixture was cooled to about 8° C. Acetic acid (22.5 g, 0.38 mol) was charged to the reactor followed by sodium hydroxide solution (28.9 g, 0.34 mol) in water (11 ml) over 0.25 hour. The reaction was cooled to 5° C. and acetone dicarboxylic acid (50.7 g, 0.34 mol) was added in one portion via a powder funnel. A solution of difluoroethylamine hydrochloride (21.7 g, 0.16 mol) in water (50 ml) was charged to a dropping funnel. SILCOLAPSE M5020™ anti-foaming agent (3 drops) was added to the reaction mass and the amine solution was added to the reaction mixture quickly, keeping the temperature below 5° C. The mixture was stirred at 0–5° C. for 1 hour, allowed to warm to ambient and then allowed to stand overnight.

The pH of the reaction mass was adjusted to pH6.5 by addition of 47% caustic soda solution, and the aqueous was then extracted with dichloromethane (3×90 ml). The combined organic layers were extracted with hydrochloric acid (3×90 ml, 2M), the acid washings were combined and adjusted to pH7 by addition of 47% caustic soda solution. The resulting aqueous was extracted with dichloromethane (3×90 ml) and the combined organic layers were dried (MgSO$_4$). Concentration in vacuo gave 8-(2,2-difluoroethyl)-8-azabicyclo[3.2.1]-octan-3-one (28.6 g, 90% yield) as an orange oil. Distillation of the crude product (78–85° C. @ 0.2 mmHg) gave a colourless oil (80% yield).

$^1$H NMR (CDCl$_3$): δ1.60–1.80(m,2H), 2.00–2.10(m,2H), 2.25(d,2H), 2.70(dd,2H), 2.95(dt,2H), 3.60(brs,2H), 5.95(tt, 1H)ppm.

Mass spectral data: 189 (M$^+$), 160, 146, 132, 120, 96.

Step 2

A 50 ml 3-necked round bottom flask was fitted with a pressure equalised dropping funnel, bubbler and magnetic stirrer. 8-(2,2-Difluoroethyl)-8-azabicyclo[3.2.1]octan-3-one (4.82 g, 25 mmol) was charged to the reaction flask and suspended in water (5 ml). Hydrochloric acid (5 ml, 5M) was added followed by solid ammonium chloride (2.23 g, 41 mmol) and the mixture stirred until the ammonium chloride had dissolved (5 minutes). The mixture was cooled to 5° C., a solution of potassium cyanide (5.03 g, 65 mmol) in water (7.5 ml) was added over 0.25 hour then the reaction was stirred at 0° C. for 3 hour. After this time, the lower oil phase was separated from the solid precipitate/aqueous phase to give 3-cyano-3-hydroxy-8-(2,2-difluoroethyl)-8-azabicyclo[3.2.1]octane as an oil which darkened on standing (5.32 g). The product was used directly in the next step.

Step 3

An oven-dried 50 ml 3-necked round bottom flask was fitted with a reflux condenser, thermometer and magnetic stirrer and an atmosphere of nitrogen was introduced. Phosphorous oxychloride (1.9 ml, 3.16 g, 24 mmol) and pyridine (14.7 ml) were charged and the mixture then cooled to −10° C. in an acetone/Drikold™ bath. 3-Cyano-3-hydroxy-8-(2, 2-difluoroethyl)-8-azabicyclo[3.2.1]octane (2 g, assumed 9 mmol, from Step 2) was added in one portion and the resulting exotherm raised the reaction mass temperature to 55° C. The mixture was then heated to 80° C. and held at this temperature for 24 hours. The reaction mass was cooled to ambient, then added to a stirred mixture of ice/water (100 ml). The drowned out mass was made basic by addition of solid sodium carbonate (6 g) and the resulting aqueous solution was then extracted with ethyl acetate (3×100 ml). The combined organics were washed with brine (100 ml), dried (Na$_2$SO$_4$) and concentrated in vacuo to give 3-cyano-8-(2,2-difluoroethyl)-8-azabicyclo[3.2.1]oct-2-ene as a brown oil (0.41 g, 13% yield).

Mass spectral data: 198 (M$^+$), 169, 147, 132, 118, 105, 92.

Step 4

An oven-dried 10 ml round bottom flask was fitted with a reflux condenser and a magnetic stirrer and placed under an atmosphere of nitrogen. 3-Cyano-8-(2,2-difluoroethyl)-8-azabicyclo[3.2.1]oct-2-ene (0.17 g, 0.53 mmol) was charged to the reactor followed by methanol (0.25 ml) and pyridine (0.75 ml) to give a solution. Solid sodium borohydride (0.039 g, 1.03 mmol) was added in a single portion and the mixture was then heated and held at reflux for 3 hour. After cooling to ambient, the reaction mass was poured into an agitated saturated aqueous potassium dihydrogen phosphate (10 ml) solution. The aqueous solution was extracted with dichloromethane (3×10 ml) and the combined organic layers were dried (Na$_2$SO$_4$). Concentration in vacuo to give 3-cyano-8-(2,2-difluoroethyl)-8-azabicyclo-[3.2.1]octane(0.197 g, 95% yield) as a mixture of epimers (90:10 exo:endo).

$^1$H NMR (CDCl$_3$) (exo isomer): δ1.40–2.00(m,8H), 2.50–2.80(m,1H), 2.60(dt, 2H), 3.25(m,2H), 5.75(tt, 1H)ppm.

Mass spectral data: 200 (M$^+$), 171, 149, 146, 132, 121, 105.

EXAMPLE 4

This Example illustrates the preparation of 3-cyano-8-(2, 2,2-trifluoroethyl)-8-azabicyclo[3.2.1]oct-2-ene.

Step 1

A 50 ml 3-necked round bottom flask was equipped with a magnetic stirrer, thermometer and hypochlorite scrubber. 8-(2,2,2-Trifluoroethyl)-8-azabicyclo[3.2.1]octan-3-one (1.06 g, 5 mmol) was charged to the reaction flask followed by hydrochloric acid (5M, 10 ml) and the mixture was cooled to 0° C. Diethyl ether (7 g) was added and the mixture stirred for 5 minutes. Potassium cyanide (3.69 g, 55 mmol) was added portionwise to the stirred, cooled reaction mixture over 0.25 hour. After complete addition the resultant pink mixture was stirred for 3 hours at 5° C. Water (10 ml) was added, the organic layer separated and the aqueous phase extracted with diethyl ether (2×10 ml). The combined ether extracts were dried (Na$_2$SO$_4$), filtered and concentrated in vacuo (without heat) to give 3-cyano-3-hydroxy-8-(2,2,2-trifluoroethyl)-8-azabicyclo[3.2.1]octane (1.13 g) as a dark red oil which solidified on standing and this was used directly in Step 2.

Step 2

An oven-dried 25 ml 3-necked round bottom flask was fitted with a reflux condenser, thermometer and magnetic stirrer and the apparatus filled with nitrogen. Phosphorous oxychloride (1.41 g, 9.1 mmol) and pyridine (6.53 g) were charged to the flask and the mixture then cooled to −10° C. in an acetone/Drikold™ bath. 3-Cyano-3-hydroxy-8-(2,2,2-trifluoroethyl)-8-azabicyclo[3.2.1]octane (0.97 g, 4.1 mmol—assumed, prepared in Step 1) was added in one portion and the resultant exotherm raised the reaction mass temperature to 20° C. The mixture was then heated to 80° C. and held at this temperature for 24 hours, after which the reaction mixture was cooled and stirred at ambient for 18 hours. The reaction mass was poured onto ice/water (50 ml) and solid sodium carbonate was added portionwise until the mixture was adjusted to pH8. The mixture was extracted with ethyl acetate (3×30 ml), the combined extracts were dried (Na$_2$SO$_4$), filtered and concentrated in vacuo to give 3-cyano-8-(2,2,2-trifluoroethyl)-8-azabicyclo[3.2.1]oct-2-ene (0.51 g, 51% yield from 8-(2,2,2-trifluoroethyl)-8-azabicyclo[3.2.1]octan-3-one; 60:40 exo:endo cyano).

EXAMPLE 5

This Example illustrates the preparation of 3-cyano-8-(2, 2,2-trifluoroethyl)-8-azabicyclo[3.2.1]oct-2-ene.

Step 1

A 500 ml 3-necked round bottom flask was equipped with a large magnetic stirrer, thermometer and hypochlorite scrubber. 8-(2,2,2-Trifluoroethyl)-8-azabicyclo[3.2.1]octan-3-one (10.56 g, 50 mmol) was charged to the reaction flask followed by hydrochloric acid (5M, 100 ml) and the mixture was cooled to 0° C. Diethyl ether (71 g) was added and the mixture stirred for 5 minutes after which potassium cyanide (36.9 g, 550 mmol) was charged to the stirred reaction mixture portionwise over 0.5 hour. After complete addition, the resultant pink mixture was stirred for 3 hour at about 3° C. The pH of the mixture was adjusted to pH5 with hydrochloric acid (5M), water (50 ml) was added and the organic layer separated. The aqueous phase was extracted with diethyl ether (2×100 ml), and the combined organic extracts dried (Na$_2$SO$_4$) to leave a solution of 3-cyano-3-hydroxy-8-(2,2,2-trifluoroethyl)-8-azabicyclo[3.2.1]octane in diethyl ether (328 ml). A sample of this solution (45 ml) was used directly in Step 2.

Step 2

An oven-dried 100 ml 3-necked round bottom flask was fitted with a thermometer, pressure equalised dropping funnel, magnetic stirrer and short path distillation set-up and the apparatus filled with nitrogen. Phosphorous oxychloride (9.09 g, 58.7 mmol) and pyridine (15.7 g) were charged to the flask and the mixture then cooled to −10° C. in an acetone/Drikold™ bath. A solution of 3-cyano-3-hydroxy-8-(2,2,2-trifluoroethyl)-8-azabicyclo[3.2.1]octane in diethyl ether (45 ml, prepared in Step 1) was added dropwise to the reaction mixture keeping the temperature below 10° C. The mixture was then heated to 80° C. and the diethyl ether (about 40 ml) was distilled out. The condenser was re-arranged to reflux and the reaction was held at 80° C. for 24 hours after which it was cooled and stirred at ambient for 18 hours. The reaction mass was poured onto ice/water (50 ml) and sodium carbonate was added portionwise until the mixture was adjusted to pH8. The mixture was extracted with ethyl acetate (3×30 ml) and the combined extracts were washed with water(200 ml) and brine (200 ml). The extracts were dried ($Na_2SO_4$), filtered and concentration in vacuo to give 3-cyano-8-(2,2,2-trifluoroethyl)-8-azabicyclo[3.2.1]-oct-2-ene (1.16 g, 60% yield from 8-(2,2,2-trifluoroethyl)-8-azabicyclo[3.2.1]octan-3-one; 73:27 exo:endo cyano).

EXAMPLE 6

This Example illustrates the preparation of 3-cyano-8-(2,2,2-trifluoroethyl)-8-azabicyclo[3.2.1]oct-2-ene.

Step 1

A 500 ml 3-necked round bottom flask was equipped with an overhead paddle stirrer, thermometer and hypochorite scrubber. 8-(2,2,2-Trifluoroethyl)-8-azabicyclo[3.2.1]octan-3-one (10.82 g, 50 mmol) was charged to the reaction flask followed by hydrochloric acid (5M, 100 ml) and the mixture was cooled to 0° C. Diethyl ether (70.8 g, 955 mmol) was added and the mixture stirred for 5 minutes. Potassium cyanide (36.9 g, 550 mmol) was added to the stirred reaction mixture portionwise over 0.5 hour. After complete addition the resultant pink mixture was stirred for 3 hour at about 3° C. The pH of the mixture was adjusted to 5.8 using hydrochloric acid (5M), water (50 ml) was added and the pH re-adjusted from 7 to 5.8. The organic layer was separated off and the aqueous phase was extracted with diethyl ether (2×100 ml). The ether extracts were combined, washed with highly dilute (pH 5.6) hydrochloric acid to leave a solution of 3-cyano-3-hydroxy-8-(2,2,2-trifluoroethyl)-8-azabicyclo[3.2.1]octane in diethyl ether (303 ml).

A portion of the solution (140 ml) was treated with sulphuric acid (3 drops of 98%), dried ($MgSO_4$), and concentrated in vacuo to give 3-cyano-3-hydroxy-8-(2,2,2-trifluoroethyl)-8-azabicyclo[3.2.1]octane as a pale pink solid (4.3 g). This material was used directly in Step 2.

Step 2

A dry 25 ml 3-necked round bottom flask was fitted with a reflux condenser, thermometer and magnetic stirrer and the apparatus was filled with a nitrogen atmosphere. Phosphorous oxychloride (1.34, 8.7 mmol) and pyridine (6.22 g) were charged to the flask and the mixture then cooled to −10° C. in an acetone/Drikold™ bath. 3-Cyano-3-hydroxy-8-(2,2,2-trifluoroethyl)-8-azabicyclo[3.2.1]octane (0.92 g, 3.9 mmol—assumed, prepared in Step 1) was added in one portion and the resultant exotherm raised the reaction mass temperature to 12° C. The mixture was heated to 80° C. and held at this temperature for 23 hours after which the mixture was cooled to ambient. The reaction mixture was poured onto ice/water (50 ml) and sodium carbonate added portionwise until the mixture was adjusted to pH8. The resulting mixture was extracted with ethyl acetate (3×30 ml), the combined extracts were dried ($Na_2SO_4$), filtered and concentrated in vacuo to give 3-cyano-8-(2,2,2-trifluoroethyl)-8-azabicyclo[3.2.1]oct-2-ene (0.8 g, 72% yield from 8-(2,2,2-trifluoroethyl)-8-azabicyclo[3.2.1]-octan-3-one; 74:26 exo:endo cyano).

EXAMPLE 7

This Example illustrates the preparation of 3-cyano-3-hydroxy-8-(2,2,2-trifluoroethyl)-8-azabicyclo[3.2.1]octane.

A split-neck jacketed reactor was set up without the lid. To this was charged ground sodium cyanide (7.57 g, 154.5 mmol), followed by 8-(2,2,2-trifluoroethyl)-8-azabicyclo-[3.2.1]octan-3-one (21.1 g, 96.6 mmol) and n-butanol (48 ml), ensuring that all the sodium cyanide was washed into the reactor. The lid of the reactor was fitted (equipped with overhead paddle stirrer and thermometer) and the reactor was vented to a hypochorite scrubber. The reaction mixture was agitated and the contents cooled to 0° C. (recirculating glycol). Hydrochloric acid (5M, 26.7 ml, 133.9 mmol) was added to the reaction mixture via a syringe pump over 2.5 hours. After complete addition, the reaction was stirred for a further 0.75 hours. The pH of the mixture was adjusted from 9.5 to 3 using hydrochloric acid (5M), water (200 ml) was added, and the pH of the mixture was further adjusted to pH 1. The n-butanol layer was then separated off.

The acidic aqueous layers were transferred to a 3-necked round bottom flask equipped with an overhead paddle stirrer, thermometer, pH probe and pressure equalised dropping funnel. Toluene (100 ml) was charged to the reactor and the resultant 2 phase mixture was agitated vigorously. The pH of the mixture was adjusted from 0.7 to 5.2 by the dropwise addition of saturated sodium bicarbonate solution over 0.25 hours. The organic layer was separated and the aqueous phase was extracted with toluene (2×100 ml). Sulphuric acid (98%, 5 drops) was added to the combined toluene extracts, before drying ($MgSO_4$) and filtering. A further 5 drops of sulphuric acid were added then the toluene extracts were concentrated in vacuo to give the title compound as an off-white solid (17.0 g, 65% yield; 65:35 exo:endo cyano).

EXAMPLE 8

This Example illustrates the preparation of 3-cyano-3-hydroxy-8-(2,2,2-trifluoroethyl)-8-azabicyclo[3.2.1]octane.

A split-neck jacketed reactor was set up without the lid. To this was charged ground sodium cyanide (3.74 g, 76.3 mmol), followed by 8-(2,2,2-trifluoroethyl)-8-azabicyclo-[3.2.1]octan-3-one (10.0 g, 47.7 mmol) and n-butanol (24ml), ensuring that all the sodium cyanide was washed into the reactor. The lid of the reactor was fitted (equipped with overhead paddle stirrer and thermometer) and the reactor was vented to a hypochorite scrubber. The reaction mixture was agitated and the contents cooled to −10° C. (recirculating glycol). Hydrochloric acid (5M, 13.3 ml, 66.6 mmol) was added to the reaction mixture via a dropping funnel over 5–10 minutes. After complete addition, the reaction was stirred for 21 hours. The pH of the mixture was adjusted from 9 to 3 using hydrochloric acid (5M), water. was added (100 ml), and the pH of the mixture was further adjusted to pH1. The n-butanol layer was then separated off.

The acid washings were transferred to a 3-necked round bottom flask equipped with an overhead paddle stirrer, thermometer, pH probe and pressure equalised dropping funnel. Toluene (50 ml) was charged to the reactor and the resultant 2 phase mixture was agitated vigorously. The pH of the mixture was adjusted from 0.5 to 5.2 by the dropwise addition of saturated sodium bicarbonate solution over 0.25 hours. The organic layer was separated and the aqueous phase was extracted with toluene (2×50 ml). Sulphuric acid (98%, 3 drops) was added to the combined toluene extracts before drying (MgSO$_4$) and filtering. A further 3 drops of sulphuric acid were added after which the toluene extracts were concentrated in vacuo to give the title compound as an off-white solid (8.6 g, 69% yield; 67:33 exo:endo cyano).

EXAMPLE 9

This Example illustrates the preparation of 3-cyano-3-hydroxy-8-(2,2,2-trifluoroethyl)-8-azabicyclo[3.2.1]octane.

A split-neck jacketed reactor was set up without the lid. To this was charged round sodium cyanide (3.74 g, 76.3 mmol), followed by 8-(2,2,2-trifluoroethyl)-8-azabicyclo-[3.2.1]octan-3-one (10.1 g, 48.3 mmol) and toluene (24 ml), ensuring that all the sodium cyanide was washed into the reactor. The lid of the reactor was fitted (equipped with overhead paddle stirrer and thermometer) and the reactor was vented to a hypochorite scrubber. The reaction mixture was agitated and the contents cooled to 0° C. (recirculating glycol). Hydrochloric acid (5M, 13.3 ml, 66.6 mmol) was added to the reaction mixture via a syringe pump over 4 hours. After complete addition, the reaction was stirred for a further 44 hours. The pH of the mixture was adjusted from 9 to 5.5 using hydrochloric acid (5M), and the organic layer was separated. The aqueous phase was extracted with toluene (2×30 ml) and the combined organic extracts were washed with dilute hydrochloric acid (30 ml, pH 6). Sulphuric acid (98%, 3 drops) was added to the toluene extracts before drying (MgSO$_4$) and filtering. A further 3 drops of sulphuric acid were added before the toluene extracts were concentrated in vacuo to give the title compound as an off-white solid (8.4 g, 52% yield; 57:43 exo:endo cyano).

EXAMPLE 10

This Example illustrates the preparation of 3-cyano-3-hydroxy-8-(2,2,2-trifluoroethyl)-8-azabicyclo[3.2.1]octane.

A split-neck jacketed reactor was set up without the lid. To this was charged (unground) sodium cyanide (3.90 g, 77.3 mmol), followed by 8-(2,2,2-trifluoroethyl)-8-azabicyclo[3.2.1]octan-3-one (10.1 g, 48.3 mmol), methyl tert-butyl ether (24 ml) and water (10 ml), ensuring that all the sodium cyanide was washed into the reactor. The lid of the reactor was fitted (equipped with overhead paddle stirrer and thermometer) and the reactor was vented to a hypochorite scrubber. The reaction mixture was agitated and the contents cooled to 0° C. (recirculating glycol). Concentrated hydrochloric acid (5.73 ml, 67.1 mmol) was added to the reaction mixture via a syringe pump over 4 hours. After complete addition, the reaction was stirred for a further 28 hours. The pH of the mixture was adjusted from 9 to 5.5 using hydrochloric acid (5M) and the organic layer was separated. The aqueous phase was extracted with diethyl ether (2×30 ml) and the combined organic extracts were washed with dilute hydrochloric acid (30 ml, pH 6). Sulphuric acid (98%, 3 drops) was added to the ether extracts before drying (MgSO$_4$) and filtering. A further 3 drops of sulphuric acid were added to the ether extracts after which they were concentrated in vacuo to give the title compound as an off-white solid (8.1 g, 64% yield; 58:42 exo:endo cyano).

EXAMPLE 11

This Example illustrates the preparation of 3-cyano-3-hydroxy-8-(2,2,2-trifluoroethyl)-8-azabicyclo[3.2.1]octane.

A split-neck jacketed reactor was equipped with a stirrer bar, thermometer, hypochorite scrubber and pressure equalised dropping funnel. To this was charged 8-(2,2,2-trifluoroethyl)-8-azabicyclo[3.2.1]octan-3-one (3.04 g, 14.5 mmol) and butyl acetate (7 ml). The reaction mixture was agitated and cooled to 0° C. (recirculating glycol), then ground sodium cyanide (1.07 g, 21.7 mmol) was added via a powder funnel. Hydrochloric acid (5M, 4.0 ml, 20.3 mmol) was added to the reaction mixture via a dropping funnel over 5 minutes after which the reaction mixture was stirred for 29 hours. The pH of the reaction was adjusted from 9 to 5.5 using hydrochloric acid (5M) and the organic layer was separated. The aqueous phase was extracted with diethyl ether (2×30 ml) and the combined organic extracts were washed with dilute hydrochloric acid (30 ml, pH 6). Sulphuric acid (98%, 2 drops) was added to the extracts before they were dried (MgSO$_4$) and filtered. A further 2 drops of sulphuric acid were added and then the ether was removed in vacuo to give a solution of the title compound in butyl acetate.

EXAMPLE 12

This Example illustrates the preparation of 3-cyano-3-hydroxy-8-(2,2,2-trifluoroethyl)-8-azabicyclo[3.2.1]octane.

A split-neck jacketed reactor was equipped with a stirrer bar, thermometer, hypochlorite scrubber and pressure equalised dropping funnel. To this was charged 8-(2,2,2-trifluoroethyl)-8-azabicyclo[3.2.1]octan-3-one (3.04 g, 14.5 mmol) and diethyl ether (7 ml). The reaction mixture was agitated and cooled to 0+ C. (recirculating glycol), then around sodium cyanide (1 .07 g, 21.7 mmol) was added via a powder funnel. Hydrochloric acid (5M, 4.0 ml, 20.3 mmol) was added to the reaction mixture via a dropping funnel over 5 minutes and the reaction mixture was then stirred for 24 hours. The pH of the mixture was adjusted from 9 to 5.5 using hydrochloric acid (5M), and the organic layer was separated. The aqueous phase was extracted with diethyl ether (2×30 ml) and the combined organic extracts were washed with dilute hydrochloric acid (30 ml, pH 6). Sulphuric acid (98%, 2 drops) was added to the extracts before drying (MgSO$_4$) and filtering. A further 2 drops of sulphuric acid were added then the ether extracts were concentrated in vacuo to give 3-cyano-3-hydroxy-8-(2,2,2-trifluoroethyl)-8-azabicyclo[3.2.1]octane ( 72:28 exo:endo cyano) as a pale yellow solution in diethyl ether. (Reaction conversion 83% by $^1$H NMR analysis.)

EXAMPLE 13

This Example illustrates the preparation of 3-cyano-3-hydroxy-8-(2,2,2-trifluoroethyl)-8-azabicyclo[3.2.1]octane.

A split-neck jacketed reactor was equipped with a stirrer bar, thermometer, hypochlorite scrubber and pressure equalised dropping funnel. To this was charged 8-(2,2,2-trifluoroethyl)-8-azabicyclo[3.2.1]octan-3-one (3.04 g, 14.5 mmol) and fluorobenzene (7 ml). The reaction mixture was agitated and cooled to 0° C. (recirculating glycol), then ground sodium cyanide (1.07 g, 21.7 mmol) was added via a powder funnel. Hydrochloric acid (5M, 4.0 ml, 20.3 mmol) was added to the reaction mixture via a dropping funnel over 5 minutes and the reaction then stirred for a further 3 hours. $^1$H NMR analysis indicated a reaction conversion of 14% to 3-cyano-3-hydroxy-8-(2,2,2-trifluoroethyl)-8-azabicyclo[3.2.1]octane.

EXAMPLE 14

This Example illustrates the preparation of 3-cyano-3-hydroxy-8-(2,2,2-trifluoroethyl)-8-azabicyclo[3.2.1]octane.

To a split-neck jacketed reactor equipped with an overhead turbine agitator, thermometer and hypocelorite scrubber was charged 8-(2,2,2-trifluoroethyl)-8-azabicyclo-[3.2.1]octan-3-one (10.89 g, 50.0 mmol), methanol (14 ml) and acetic acid (4.2 g, 70.0 mmol). The reaction mixture was cooled to 5° C. (recirculating glycol), then ground potassium cyanide (5.37 g, 80.0 mmol) was added portionwise via a powder funnel over 10 minutes. After complete addition the reaction was stirred and reaction's progress was monitored by $^1$H NMR. After a total reaction time of 44 hours NMR showed an 84% conversion to the title compound (45:55 exo:endo cyano).

EXAMPLE 15

This Example illustrates the preparation of 3-cyano-3-hydroxy-8-(2,2,2-trifluoroethyl)-8-azabicyclo[3.2.1 ]octane.

To a split-neck jacketed reactor equipped with an overhead turbine agitator, thermometer and hypochlorite scrubber was charged 8-(2,2,2-trifluoroethyl)-8-azabicyclo[3.2.1]octan-3-one (21.8 g, 100.0 mmol), methanol (28 ml) and ground potassium cyanide (10.42 g, 160.0 mmol). The reaction mixture was cooled to 5° C. (recirculating glycol), then acetic acid (4.2 g, 70.0 mmol) was added via a syringe pump over 3.5 hours. The reaction mixture was poured onto hydrochloric acid (5M, 8 ml, 0.4 molar equivalents) with agitation and cooling (ice/water). To the resultant mixture was added a further portion of hydrochloric acid (5M, 2 ml, 0.1 molar equivalents) and toluene (25 ml) and water (25 ml). The organic layer was separated and the aqueous extracted with toluene (2×25 ml). Sulphuric acid (98%, 4 drops) was added to the combined organic extracts before drying (MgSO$_4$) and filtering. A further 4 drops of sulphuric acid were added to the toluene extracts after which they were concentrated in vacuo to give the title compound as an off-white solid (20 g, 74% yield; 60:40 exo:endo cyano).

EXAMPLE 16

This Example illustrates the preparation of 3-cyano-3-hydroxy-8-(2,2,2-trifluoroethyl)-8-azabicyclo[3.2.1]octane.

A split-neck jacketed reactor was equipped with an overhead turbine agitator, thermometer and hypochlorite scrubber. To this was charged 8-(2,2,2-trifluoroethyl)-8-azabicyclo[3.2.1]octan-3-one (10.56 g, 50.0 mmol) and methanol (12 ml) after which the contents of the reactor were cooled to 5° C. (recirculating glycol) with agitation. Acetic acid (4.2 g, 70.0 mmol) was added cautiously to the reaction mixture, followed by the portionwise addition of sodium cyanide (4.80 g, 95.0 mmol) via a powder funnel over lO minutes. The reaction was then stirred for 44 hours. Excess acetic acid was added to the reaction mixture which was then stirred for 16 hours. Toluene (20 ml) and water (20 ml) were added to the reaction mixture, before concentrating in vacuo (35° C.) to remove methanol. The residue was extracted with toluene (3×20 ml) and the combined organic extracts were washed with dilute hydrochloric acid (30 ml, pH 6). Sulphuric acid (98%, 2 drops) was added to the toluene extracts before drying (MgSO$_4$) and filtering. A further 3 drops of sulphuric acid were added after which the toluene extracts were concentrated in vacuo to give the title compound as a pale brown semi-solid (4 g, 64% yield; 50:50 exo:endo cyano).

EXAMPLE 17

This Example illustrates the preparation of 3-cyano-8-(2,2,2-trifluoroethyl)-8-azabicyclo[3.2.1]oct-2-ene.

A 3-necked round bottom flask was equipped with an overhead paddle stirrer, thermometer, condenser, nitrogen atmosphere and hypochlorite scrubber. To this was charged phosphorous oxychloride (12.4 ml, 0.13 mol) followed by pyridine (97 ml, 1.20 mol) and the mixture was cooled to −5° C. 3-Cyano-3-hydroxy-8-(2,2,2 trifluoroethyl)-8-azabicyclo[3.2.1]-octane (14.0 g) was added in one portion and the resultant exotherm raised the temperature of the reaction mixture to 8° C. The mixture was then heated to 80–88° C. and held at that temperature for 24 hours before cooling to ambient. The reaction mixture was poured onto ice/water (200 ml), then saturated sodium carbonate solution was added cautiously and the mixture was adjusted to about pH 8. The mixture was extracted with ethyl acetate (3×200 ml), the combined extracts were dried (Na$_2$SO$_4$), filtered and concentrated in vacuo to give the title compound (11.5 g).

The product was purified by column chromatography (silica, dichloromethane) followed by Kugelrohr distillation (0.1 mmHg, 125≦150° C.) to give the title compound as a white crystalline solid (7.2 g, 99% purity).

EXAMPLE 18

This Example illustrates the preparation of 3-cyano-8-(2,2,2-trifluoroethyl)-8-azabicyclo[3.2.1]octane.

A 3-necked round bottom flask equipped with an overhead stirrer was set up for hydrogenation. The reaction flask was purged with nitrogen for 0.25 hours after which palladium on carbon catalyst (5%, 50% paste with water, 0.125 g, 0.03 mmol) was added followed by a solution of 3cyano-8-(2,2,2,-trifluoroethyl)-8-azabicyclo[3.2.1]oct-2-ene (0.50 g, 2.26 mmol) in toluene (25 ml). The reaction vessel was purged with nitrogen and then with hydrogen. The reaction mixture was agitated under hydrogen at room temperature for 3 hours, then left unstirred under nitrogen for a further 16 hours. The catalyst was removed by filtration through CELITE™ (under nitrogen atmosphere) and the filtrate was concentrated in vacuo to give the title compound (0.171 g) as a mixture of epimers (88:13 axial:equatorial). The product was a pale yellow oil which solidified on standing.

EXAMPLE 19

This Example illustrates the preparation of 3-cyano-8-(2,2,2-trifluoroethyl)-8-azabicyclo[3.2.1]octane.

A 3-necked round bottom flask equipped with an overhead stirrer was set up for hydrogenation. The flask was purged with nitrogen for 0.25 hours after which palladium on carbon catalyst (5%, 50% paste with water, 0.068 g, 0.016 mmol) was added followed by a solution of 3-cyano-8-(2,2,2,-trifluoroethyl)-8-azabicyclo[3.2.1]oct-2-ene (3.40 g, 14.9 mmol), in toluene (19 ml). The reaction vessel was purged with nitrogen and then with hydrogen. The reaction mixture was agitated at room temperature under hydrogen for 5.5 hours, then left unstirred under nitrogen for a further 16 hours.

A further portion of catalyst (0.070 g, 0.017 mmol) was then added followed by toluene (1 ml) and methanol (1ml). The reaction vessel was agitated under hydrogen for a further 4.5 hours then left unstirred under nitrogen for 16 hours. Further toluene (3 ml) was added and the reaction was agitated under hydrogen for a further 5 hours after which it was left unstirred under nitrogen for 3 days. Further toluene (19 ml) and methanol (1 ml) were added and the reaction mixture was agitated under hydrogen for a further 7 hours before leaving unstirred under nitrogen for 16 hours. A further portion of catalyst was added (0.136 g, 0.032 mmol), and the reaction mixture was agitated for a further 7 hours, before leaving it unstirred under nitrogen for 24 hours. The catalyst was removed by filtration through CELITE™

(under nitrogen atmosphere), and the filtrate was concentrated in vacuo to give the title compound (2.91 g, yellow oil, 82% crude yield) as a mixture of epimers (85:15 axial:equatorial).

EXAMPLE 20

This Example illustrates the preparation of 3-cyano-8-(2, 2,2-trifluoroethyl)-8-azabicyclo[3.2.1]octane.

To a 3-necked round bottom flask equipped with an overhead stirrer and set up for hydrogenation were charged 3-cyano-8-(2,2,2,-trifluoroethyl)-8-azabicyclo[3.2.1]oct-2-ene (0.50 g, 2.26 mmol) and ethanol (35 ml). After the reaction vessel had been purged with nitrogen palladium on carbon catalyst (5%, 0.025 g, 0.012 mmol) in water (0.5 ml) was added. The reaction vessel was purged with nitrogen and then with hydrogen. The reaction mixture was agitated at room temperature for 10.5 hours, before removing the catalyst by filtration through CELITE™ (under nitrogen atmosphere). The filtrate was concentrated in vacuo to give the title compound as an off-white crystalline solid (0.47 g, 69% reaction conversion) as a mixture of epimers (80:20 axial:equatorial). The isolated product was redissolved in ethanol and hydrogenation was continued.

The partially hydrogenated mixture and ethanol (35 ml) were charged to a reaction vessel and the vessel was purged with nitrogen. Palladium on carbon catalyst (5%, 0.025 g, 0.012 mmol) in water (0.5 ml) was added. The reaction vessel was purged with nitrogen and then with hydrogen. The reaction mixture was agitated at room temperature for 4 hours before removing the catalyst by filtration through CELITE™ (under nitrogen atmosphere). The filtrate was concentrated in vacuo to give the title compound as an off-white crystalline solid (0.45 g, 100% reaction conversion) as a mixture of epimers (57:43 endo:exo).

EXAMPLE 21

This Example illustrates the preparation of 3-cyano-8-(2, 2,2-trifluoroethyl)-8-azabicyclo[3.2.1]oct-2-ene.

A 3-necked round bottom flask was equipped with a magnetic stirrer, thermometer, condenser, nitrogen atmosphere and scrubber. To this was charged thionyl chloride (2.1 ml, 0.028 mol) followed by pyridine (4.46 ml, 0.055 mol). 3-Cyano-3-hydroxy-8-(2,2,2 trifluoroethyl)-8-azabicyclo[3.2.1]-octane (5.05 g, 0.021 mol) was added, followed by chloroform (20 ml) and the resultant exotherm raised the temperature of the reaction mixture to 50° C. The mixture was stirred at ambient for 1 hour, at 55° C. for 1 hour and was then refluxed for 1 hr. Additional thionyl chloride (2.1 ml, 0.028 mol) and pyridine (4.46 ml, 0.055 mol) were charged and the mixture then stirred at ambient for a further 1 hour.

The reaction mass was poured slowly onto ice/saturated sodium carbonate solution (200 ml) and the pH was adjusted to pH6 by addition of further bicarbonate solution. The organic layer was separated and the aqueous phase was extracted with dichloromethane (3×150 ml). The combined extracts were dried (MgSO$_4$), filtered and concentrated in vacuo to give the title compound (3.5 g, 47% yield).

EXAMPLE 22

This Example illustrates the preparation of 3-cyano-8-(2, 2,2-trifluoroethyl)-8-azabicyclo[3.2.1]octane.

3-Cyano-8-(2,2,2-trifluoroethyl)-8-azabicyclo[3.2.1]oct-2-ene (1 g 4.6 mmol), toluene (8 ml) and 5% palladium on carbon (0.02 g; Johnson Matthey type 87L powder) were charged to a stainless steel hydrogenation vessel (25 ml). The vessel was sealed, purged with nitrogen and the nitrogen replaced with hydrogen at 3 bar pressure. The vessel was left for 10 minutes without stirring to ensure there was no leakage of gas. The hydrogen was vented from the system, the reaction mixture heated to 50° C. with stirring (350 rpm) and the vessel pressurised (400 psi) with hydrogen. There was no indication of gas uptake after 1 hour but the reaction mixture was left stirring for 12 hours and then static left overnight.

The vessel was vented, purged with nitrogen, and sampled for gas chromatographic analysis which showed there to be 96% 3-cyano-8-(2,2,2-trifluoroethyl)-8-azabicyclo[3.2.1]-oct-2-ene. More palladium on carbon catalyst (0.02 g) was added to the reaction, the vessel was repressurised and reheated to 50° C. After an induction period of 1 hour the hydrogen uptake started with 75 ml of hydrogen being absorbed in 2 hours. Heating and stirring were continued for a further 5 hours and then stopped. The reaction mixture was allowed to stand overnight. The reaction mixture was filtered to remove the catalyst and the filtrate evaporated under reduced pressure with a bath temperature of 50° C. The last traces of solvent were removed under oil pump pressure to give the title compound as a colourless oil (yield 890 mg, endo cyano 76%, exo cyano 20%).

EXAMPLE 23

This Example illustrates the preparation of 3-exo-cyano-3-endo-hydroxy-8-(2,2,2-trifluoroethyl)-8-azabicyclo [3.2.1]octane (that is, equatorial cyano).

A 250 ml jacketed flask was equipped with overhead stirrer, thermometer and vented to a hypochlorite scrubber. The flask was cooled to 0° C. using a Haake recirculating bath, before charging aqueous hydrochloric acid (5M, 96.6 ml, 483 mmol), along with sodium cyanide (26.82 g, 531 mmol). The pH was adjusted to 9.0 with further hydrochloric acid before charging 8-(2,2,2-trifluoroethyl)-8-azabicyclo [3.2.1]octan-3-one (20.4 g, 97 mmol) over 1 ½ hours. Precipitation of product accompanied the addition. After a further ½ hour, the pH had changed to 8.3 and further sodium cyanide (4.5 g) was added to bring pH to 9.1. Stirring was continued overnight at 0° C. Water (100 ml) was added, and the pH adjusted to 5.0 with hydrochloric acid. The light brown precipitate that had formed was collected by filtration, then taken up in methyl tert-butyl ether (100 ml) and sulphuric acid (98%, 3 drops) was added to stabilise product. A small amount of brown aqueous material was decanted from the organic solution, which was concentrated under reduced pressure to give 5.2 g brown crystals (22% yield at 96% strength) of the title compound.

EXAMPLE 24

This Example illustrates the preparation of 3-exo-cyano-3-endo-hydroxy-8-(2,2,2-trifluoroethyl)-8-azabicyclo [3.2.1]octane (that is, equatorial cyano).

A 250 ml split neck jacketed reactor was equipped with overhead stirrer, thermometer, and vented to a hypochlorite scrubber. To the reactor was charged water (50 ml), followed by sodium cyanide (13.42 g, 265 mmol) and the solution was cooled to 0° C. 8-(2,2,2-Trifluoroethyl)-8-azabicyclo[3.2.1] octan-3-one (5.0 g, 24 mmol) and concentrated hydrochloric acid (22.1 g, 221 mmol) were mixed and the resultant brown hydrochloride solution was charged to the reactor over 1.25 hour (via syringe pump). A cream coloured precipitate formed during the addition. The reaction mixture was agitated overnight, then the pH was adjusted from pH 8.7 to pH 4.8 using hydrochloric acid. Diethyl ether (40 ml) was added (the pH fell to 2 and was re-adjusted to 5.6 with 70% sodium hydroxide). The organic phase was separated off and the aqueous extracted with a further portion of diethyl ether (40 ml). The combined organic extracts were washed with pH 5.5 water (modified with hydrochloric acid), stabilised (2 drops sulphuric acid), dried (MgSO$_4$), filtered, re-stabilised and concentrated under reduced pressure to give a brown water-wet semi-solid. The material was re-dissolved in diethyl ether, dried (MgSO$_4$), filtered, stabilised and concentrated under reduced pressure to give the title compound as a pale brown solid (3.0 g, 85% strength, 45% yield).

EXAMPLE 25

This Example illustrates the conversion of a mixture of axial/equatorial cyano 3-cyano-3-hydroxy-8-(2,2,2-trifluoroethyl)-8-azabicyclo[3.2.1]octane and 8-(2,2,2-trifluoroethyl)-8-azabicyclo[3.2.1]octan-3-one to a mixture of 3-exo-cyano-3-endo-hydroxy-8-(2,2,2-trifluoroethyl)-8-azabicyclo[3.2.1]octane (that is, equatorial cyano only) and 8-(2,2,2-trifluoroethyl)-8-azabicyclo[3.2.1]octan-3-one.

A 50 ml split-neck jacketed reactor was equipped with an overhead stirrer, thermometer and was vented to a hypochlorite scrubber. To this was charged sodium cyanide (0.75 g, 14.9 mmol), sodium chloride (1.15 g, 19.7 mmol), hydrochloric acid (5M, 2.12 g, 0.49 mmol) and water (16 ml). The reaction mixture was cooled to 0° C. (Haake recirculating unit) with agitation and a mixture of axial/equatorial cyano 3-cyano-3-hydroxy-8-(2.2,2-trifluoroethyl)-8-azabicyclo [3.2.1]octane(cyanohydrin) and 8-(2,2,2-trifluoroethyl)-8-azabicyclo[3.2.1]octan-3-one (tropinone) (5.0 g) was charged to the reactor in one portion. Reaction progress was monitored by $^1$H NMR and progress is presented in the table below. After 18 hours stirring at 0° C. the pH of the reaction mixture was adjusted from 8.7 to 5.7 using hydrochloric acid. The product was filtered off at 0° C. jacketed filter), dissolved in diethyl ether and the residual water separated off from this. Sulphuric acid (98%, 2–3 drops) were added to the ethereal solution before drying (MgSO$_4$), filtering, adding further sulphuric acid (98%, 2–3 drops) and concentrating in vacuo to give the title mixture (3.8 g).

| TOTAL | COMPOSITION | | EPIMER RATIO |
|---|---|---|---|
| TIME (hr) | cyanohydrin | tropinone | equatorial cyano:axial cyano |
| 0 | 91 | 9 | 70:30 |
| 1 | 75 | 25 | 77:23 |
| 2 | 51 | 49 | 74:26 |
| 20 | 58 | 42 | 100:0 |

EXAMPLE 26

This Example illustrates the preparation of 3-cyano-8-(2,2,2-trifluoroethyl)-8-azabicyclo[3.2.1]oct-2-ene.

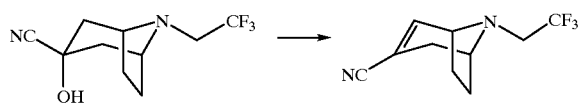

A 50 ml 3-necked round bottom flask was equipped with overhead stirrer, thermometer, nitrogen blanket, and vented to a hypochlorite scrubber. To the reactor was charged 3-exo-cyano-3-endo-hydroxy-8-(2,2,2-trifluoroethyl)-8-azabicyclo[3.2.1]octane (2 g, 8.55 mmol), in acetonitrile (20 ml), followed by thionyl chloride (1.88 ml, 25.6 mmol) and pyridine (1.67 ml, 20.5 mmol). After stirring for 2¼ hours, the reaction mixture was quenched by the cautious addition of water (10 ml), with cooling via a water bath. The pH was adjusted from 0.1 to 8 by addition of aqueous sodium hydroxide solution (70%, 8.5 ml) before extraction with dichloromethane (2×25 ml). The extracts were combined, washed with water (25 ml), dried (MgSO$_4$), filtered and concentrated under reduced pressure to give the title compound as a brown oil (1.92 g, 76% strength, 84% yield, racemic mixture).

EXAMPLE 27

This Example illustrates the use of different amines, solvents and stoichiometries, while using thionyl chloride, for the preparation of 3-cyano-8-(2,2,2-trifluoroethyl)-8-azabicyclo[3.2.1]oct-2-ene by dehydrating 3-exo-cyano-3-endo-hydroxy-8-(2,2,2-trifluoroethyl)-8-azabicyclo[3.2.1] octane.

General Procedure

Thionyl chloride (305 mg, 2.6 mmol) in 1 ml acetonitrile was added to a tube containing an amine (0.25–2.5 equivalents). 3-exo-Cyano-3-endo-hydroxy-8-(2,2,2-trifluoroethyl)-8-azabicyclo[3.2.1 ]octane (300 mg, about 50% strength, 0.64 mmol) was then added as a solution in acetonitrile (2 ml), and reaction mixture stirred at ambient temperature. A sample (¾ml) was added to aqueous sodium hydroxide (3 ml, 0.5M), the resulting mixture was extracted with ethyl acetate (3 ml) and the organic layer analysed by gas chromatography (gc). Results are presented in the table below and percentage conversion to 3-cyano-8-(2,2,2-trifluoroethyl)-8-azabicyclo[3.2.1]oct-2-ene (Product) is shown.

| Amine | Amount of amine (equivalents) | Time (hours) | Percentage conversion to Product |
|---|---|---|---|
| Pyridine | 0.25 | 12 | 11 |
| Pyridine | 1.1 | ½ | 30 |
| Pyridine | 1.1 | 2 | 65 |
| Pyridine | 2.5 | ½ | 58 |
| Pyridine | 2.5 | 2 | 91 |
| Quinoline | 0.25 | ½ | 17 |
| Quinoline | 0.25 | 2 | 22 |
| Quinoline | 1.1 | ½ | 35 |
| Quinoline | 1.1 | 2 | 60 |
| Quinoline | 2.5 | ½ | 59 |
| Quinoline | 2.5 | 2 | 95 |
| Triethylamine | 2.5 | 12 | 66 |
| Diisopropylethylamine | 0.25 | 12 | 15 |
| N,N-Dimethylaniline | 0.25 | ½ | 12 |
| 4-Dimethylaminopyridine | 1.1 | ½ | 26 |
| 4-Dimethylaminopyridine | 1.1 | 72 | 32 |
| 4-Dimethylaminopyridine | 2.5 | ½ | 71 |
| 4-Dimethylaminopyridine | 2.5 | 72 | 78 |

EXAMPLE 28

This Example illustrates the preparation of 3-cyano-8-(2,2,2-trifluoroethyl)-8-azabicyclo[3.2.1]octane.

Palladium on carbon catalyst (5%, Johnson Matthey Type 87 L powder, 0.02 g, 0.018 mmol), 3-cyano-8-(2,2,2-trifluoroethyl)-8-azabicyclo[3.2.1]oct-2-ene (2.91 g, 0.013 mmol) and toluene (8 ml) were charged to a 25 ml stainless steel Parr™ reactor and the vessel was sealed. The apparatus was purged with nitrogen 3 times and the nitrogen was replaced with hydrogen at 3 bar pressure. The vessel was left for 10 minutes without stirring to ensure no leakage of gas. Hydrogen was vented from the system, the reaction heated to 50° C. with stirring and the vessel was re-pressurised with hydrogen to 3 bar. The vessel was left stirring at 50° C. for 12 hours (with the hydrogen uptake being monitored with a 'Pressflow' gas control unit) then allowed to cool overnight. A further portion of catalyst (0.02 g, 0.018 mmol) was added to the vessel, before purging with nitrogen and re-pressurising with hydrogen. The reaction mixture was heated to 50° C. with agitation for a further 9 hours before cooling to ambient. The reaction mixture was carefully filtered through CELITE™ to remove the catalyst and the solvent removed under reduced pressure to leave the title compound as a colourless oil (0.89 g, 85% yield, 97% strength by gc; axial:equatorial cyano isomer mixture was 79:21).

and, ii. reducing a compound of formula (III) by catalytic hydrogenation.

2. A process as claimed in claim 1 for preparing a compound of formula (IV) as defined in claim 1, comprising the steps:

Chemical Formulae used in the Description

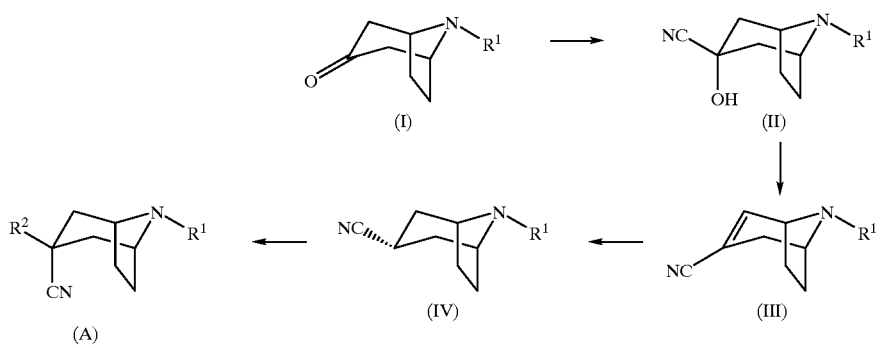

What is claimed is:

1. A process for preparing a compound of formula (IV):

i. reacting a compound of formula (I):

(I)

(IV)

wherein $R^1$ is $C_{1-4}$ alkyl, $CH_2(C_{1-3}$ haloalkyl), benzyl, $CH_2(C_{2-5}$ alkenyl) or $CH_2(CH_{2-5}$ alkynyl), which comprises the steps:

i. dehydrating a compound of formula (II):

(II)

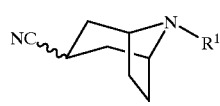

by reacting it with an acid chloride in the presence of an amine having a pKa in the range 3–11, at a temperatare in the range 0–110° C., to give a compound of formula (III):

with a mixture of an inorganic cyanide and an acid in the presence of a base, to give a compound of formula (II);

ii. dehydrating a compound of formula (II) by reacting it with an acid chloride and an amine having a pKa in the range 3–11 at a temperature in the range 0–110° C., to give a compound of formula (III); and, iii reducing a compound of formula (III) by catalytic hydrogenation.

3. A process as claimed in claim 1 for preparing a compound of formula (IV), wherein $R^1$ is as defined in claim 1 comprising the steps:

i. reacting a compound of formula (I) with a mixture of an alkali metal cyanide and a mineral acid in water at ambient temperature to give a compound of formula (II);

ii. reacting a compound of formula (II) with thionyl chloride or phosphorus oxychloride in the presence of pyridine to give a compound of formula (III); and, iii. reducing a compound of formula (II) by reacting it with hydrogen under substantially anhydrous conditions in tBe presence of a palladium on carbon catalyst at a temperature in the range 35–75° C. at a pressure in the range 2–6 bar and in the presence of an aromatic hydrocarbon solvent.

4. A process as claimed in claim 1, wherein $R^1$ is $CH_2(C_{1-3}$ haloalkyl).

5. A compound of formula (II) or (III):

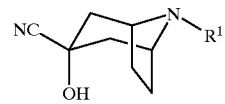

(II)

(III)

wherein $R^1$ is $CH_2(C_{1-3}$ haloalkyl).

6. A compound of formula (II) or (III) as claimed in claim 5 wherein $R^1$ is $CH_2CF_3$ or $CH_2CHF_2$.

7. A process for preparing a compound of formula (II):

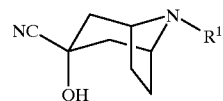

(II)

wherein $R^1$ is as defined in claim 1, comprising contacting a compound of formula (V):

(V)

with a mixture of an alkali metal cyanide and a strong mineral acid in a suitable solvent.

* * * * *